United States Patent [19]

Pez

[11] 4,409,411

[45] Oct. 11, 1983

[54] PROCESS OF HYDROGENATING BENZENES AND GROUP IVA METAL HYDRIDE CATALYSTS THEREFOR

[75] Inventor: Guido P. Pez, Boonton, N.J.

[73] Assignee: Allied Corporation, Morris Township, Morris County, N.J.

[21] Appl. No.: 303,261

[22] Filed: Sep. 17, 1981

[51] Int. Cl.³ ............................ C07C 5/02; C07C 5/03
[52] U.S. Cl. ...................................... 585/275; 585/266
[58] Field of Search ................................ 585/266, 275

[56] References Cited

U.S. PATENT DOCUMENTS

| | | | |
|---|---|---|---|
| 2,418,441 | 4/1947 | Whitman | 252/410 X |
| 3,458,547 | 7/1969 | Coffey et al. | 585/266 X |
| 3,723,560 | 3/1973 | Gleim et al. | 585/275 X |
| 4,046,790 | 9/1977 | Armor et al. | 585/275 X |
| 4,224,458 | 9/1980 | Grey et al. | 585/266 |
| 4,268,454 | 5/1981 | Pez et al. | 260/439 R |
| 4,271,323 | 6/1981 | Durand et al. | 585/275 X |

OTHER PUBLICATIONS

Zucchini, U. et al., Journal of Organometallic Chem. 26, (1971) pp. 357–372.
Lisichkin, et al., Titanium Hydride-Catalyzed Reactions of 1-Hexene 1971, *Doklady Akademii Nauk SSSR*, vol. 197, No. 1, pp. 98–100.
Lisichkin, G. V. et al., *Russ. J. Phys. Chem.*, 1972, 46(4), 620–621.
Zucchini, U. et al., *Chem. Soc. Chem. Commun.*, 1969, 1174–1175.

*Primary Examiner*—Helen M. S. Sneed
*Attorney, Agent, or Firm*—Alan M. Doernberg; Gerhard H. Fuchs

[57] ABSTRACT

Benzene, or an alkylbenzene, is hydrogenated by reaction with hydrogen in the presence of a Group IVa (titanium family) or Va metal hydride catalyst. The catalyst may be a simple hydride such as $ZrH_2$ or a hydride of an alloy such as $Cu_3Zr$ or may be a complex material. One complex material is the reaction product of a Group IVa or Va metal halide, such as $ZrCl_4$ with an alkyllithium or aryllithium, such as n-butyllithium, in a hydrocarbon solvent.

12 Claims, No Drawings

PROCESS OF HYDROGENATING BENZENES AND GROUP IVA METAL HYDRIDE CATALYSTS THEREFOR

BACKGROUND OF THE INVENTION

The present invention relates to the hydrogenation of benzene and substituted benzenes with elemental hydrogen and a solid catalyst to produce cyclohexene and substituted cyclohexenes. The present invention also relates to certain novel compounds containing group IVa metal hydrides on a carbonaceous support.

The hydrogenation of benzene and substituted benzenes is a well know reaction, typically employing various transition metals such as nickel, palladium or platinum as the catalyst. Typically, when benzene itself is hydrogenated with the nickel or group VIII metal catalyst, the product mixture is predominately or entirely cyclohexane. For many applications, such as the production of cyclohexanol, cyclohexene is the preferred product.

Group IVa metals, and especially zirconium, are well known to form hydrides which are useful either for hydrogen storage or as a moderator in a nuclear reactor. While the thermodynamics, structure and metallurgy of zirconium hydride and its alloys has been well studied for these conventional applications, the use of group IVa metal hydrides as catalysts for the hydrogenation of aromatics has not been suggested.

BRIEF DESCRIPTION OF THE INVENTION

The present invention includes a process of hydrogenating benzene or an alkylbenzene which comprises reacting liquid benzene or alkylbenzene with hydrogen gas in the presence of a solid catalyst comprising a group IVa metal hydride selected from the group consisting of zirconium hydride, titanium hydride and hafnium hydride. The present invention also includes a method of producing a carbonaceous group IVa metal hydride catalyst which comprises reacting a group IVa metal halide with a hydrocarbon solution of an alkyllithium or aryllithium, recovering the solid carbonaceous product and reacting the carbonaceous product with hydrogen. The present invention further includes the use of the carbonaceous group IVa metal hydride produced by the novel method as a catalyst for the hydrogenation of benzene or of an alkylbenzene.

DETAILED DESCRIPTION OF THE INVENTION

The process of the invention applies to the hydrogenation of either benzene or alkylbenzenes such as toluene, xylene, ethylbenzene or similar compounds of 6-12 carbons. This reactant is present as a liquid under the reaction conditions. The other reactant, hydrogen, is present as a gas under superatmospheric pressures, preferably greater than about 400 kPa, and usually in excess over the stoichmetric amount.

The catalyst for the process is a Group IVa metal hydride such as zirconium, hafnium or titanium hydride, either by itself or in an alloys or complex Example 1 below illustrates the use of single hydrides. Example 2 illustrates the preparation of a copper-zirconium alloy hydride, which is the subject of a specific invention of Guido Pez and Arnulf J. Maeland. Other alloy hydrides are contemplated such as silver-zirconium and gold-zirconium and should be active in the present process.

An especially preferred class of catalyst are the solid carbonaceous materials formed by the reaction between a group IVa metal halide and a hydrocarbon solution of an alkyllithium or aryllithium. Preferred halides are zirconium tetrachloride, zirconium trichloride, hafnium tetrachloride, titanium tetrachloride, titanium dichloride and the bromides corresponding to each of the above. Preferred hydrocarbon solvents are aliphatic hydrocarbons of 4-12 carbons such as n-hexane, aromatic hydrocarbons of 6-12 carbons such as toluene or xylene, and mixtures of such hydrocarbons. Preferred alkyllithium compounds are those with alkyl of 1-8 carbons such as methyllithium, ethyllithium, n-propyllithium, i-propyllithium, n-butyllithium, t-butyllithium, n-hexyllithium and n-octyllithium. Preferred aryllithium compounds include phenyllithium and naphthyllithium. The alkyllithium or aryllithium should preferably be chosen together with the hydrogen solvent to be miscible or soluble therein; or at least partly so. Lithium compounds with larger hydrocarbyls than those illustrated above are less preferred.

In some preferred forms, a copper halide is also reacted with the Group IVa metal halide and hydrocarbon solution of alkyllithium or aryllithium. While any copper (I) halide or copper (II) halide may be used, copper (I) halides such as CuCl and CuBr are preferred and CuCl is more preferred. It is preferred in all cases to use an excess of alkyllithium or aryllithium.

The reaction produces the desired carbonaceous material under a variety of conditions of temperature and reactant ratios, but must be conducted in the absence of reactive solvents or gases, including oxygen, ethers and amines. Elemental nitrogen may also be reactive. The reaction product contains group IVa metal (e.g. zirconium), lithium, halide (e.g. chloride), carbon and hydrogen; and the group IVa metal may be either in elemental form or as a hydride. By-product oils from the alkyl or aryl radical of the lithium compound can be removed by washing with hydrocarbon. No attempt need be made to remove lithium halide.

The carbonaceous reaction product is reacted with hydrogen to form the active catalyst. This may be done separately before introducing benzene or alkylbenzene or in situ. The product, which is a hydride, may be isolated before use or reuse.

In the hydrogenation of benzene or alkylbenzene, the necessary ingredients are catalyst, hydrogen and aromatic. No solvent is required, but compatible inert solvents such as aliphatic hydrocarbons may be used.

It is preferred that a catalyst modifier be present, such as an aliphatic tertiary amine, a dialkylether, a cycloalkylether of at least five ring carbons (i.e. not tetrahydrofuran or smaller, because such smaller cycloalkylethers have too strong a coordinating capacity and irreversibly deactivate the zirconium catalyst) and cyclic unsaturated amines. The number of carbons in the various types of co-catalysts is not critical, except when a minimum is required to avoid deactivation; and polyamines or polyethers may be used provided that such amine nitrogen is tertiary and each nitrogen or oxygen is bonded to two aliphatic carbons. The term cyclic unsaturated tertiary amines is intended to include —N— as a ring substituent in structures with one or many rings, but is not intended to include condensed polycyclics with N bonded to three carbons as a part of two rings. Suitable catalyst modifiers include methyl ether, ethyl ether, propyl ether, isopropyl ether, hexyl ether, tetrahydropyran, trimethylamine, triethylamine, tripropylamine, N-methyl piperidine and N-methyl perhydroquinoline.

EXAMPLES

All the $ZrH_x$, $HfH_x$, etc. catalysts described here are very air sensitive and were handled under argon, using a Vacuum Atmospheres drybox. It is expected that they will also react with dinitrogen ($N_2$). Solvents were carefully purified by treatment with $LiAlH_4$ followed by storage over Na/anthracene (ethers) or by prolonged contact with Na/K alloy (hydrocarbons). Matheson UHP grade hydrogen and argon were used. Volatile liquids were transferred using a glass/stainless steel, vacuum/pressure manifold. Specific examples are now given for the preparation of the various catalysts and their utilization for the systhesis of cyclohexane from benzene.

EXAMPLE 1

Catalytic Hydrogenation of Benzene using Zirconium hydride ($ZrH_2$)

A glass tubular reactor (measuring 25 mm O.D., 17.5 mm I.D.), approximately 10 cm in length, and attached to an 9 mm Kontes Teflon stopcock, was loaded with $ZrH_2$ (200 mg) (the $ZrH_2$ was obtained from ROC/RIC, or made by reaction or Zr (atomic grade) with $H_2$) and a ⅜″ (9.5 mm)×⅞″ (22.2 mm) long glass-covered magnetic stir bar. The reactor was attached to a steel vacuum/pressure manifold, evacuated and benzene (5 mL) added by distillation in vacuum. The mixture was stirred under an initial pressure of $H_2$ (900 kPa), at 82°–105° C. After an initial induction period of about 1–1.5 hours a pressure drop was noted; heating was then continued for 7 hours to a residential pressure of 748 kPa. The mixture was cooled to room temperature, then to −196° C., and the $H_2$ was removed by pumping in vacuum. Analysis of the remaining liquid by gas chromatography showed 8.2% conversion of benzene to a mixture of cyclohexene and cyclohexane with 14% selectivity to cyclohexene. (The selectivity is defined as w/w: $C_6H_{10}/(C_6H_{10}+C_6H_{12})$). The other hydrogenation reactions with binary hydrides, listed in Table 1, were done in a similar manner.

EXAMPLE 2

Preparation of a Zirconium Copper Alloy (Hydride) Catalyst

Nuclear grade zirconium (2.29819 g) was melted (under argon) together with copper (99.98% Cu, 4.80419 g), giving a pellet of nominal composition calculated as $Cu_{2.974}Zr$. (It is assumed the observed weight decrease of 0.04338 g during the melting is due to loss of copper.) The alloy pellet was loaded into a pressure vessel containing a magnetically operated dasher for grinding the contents. Hydrogen at 12.68 MPa was admitted into the pressure vessel. The material was ground under hydrogen pressure (in the range of 12.68 to 8.61 MPa) with the dasher operating at 608 strokes per minute, for a total of 4 hours. The pressure was then reduced to ambient levels, the vessel was evacuated and then filled with argon.

The product, which appeared as a hard compacted, extremely fine powder was (easily) ground and bottled under an atmosphere of pure argon. From an x-ray diffraction pattern (sample protected from air with silicone grease), the product was identified as $Cu_3Zr$. There is no evidence that this material is a metal hydride: however, because of the pulverization that took place under high hydrogen pressures it is clear that a hydride intermediate was formed under these conditions; (and that one may be formed again by admission of $H_2$).

EXAMPLE 3

Preparation of $ZrH_x$ Catalyst

An H-shaped glass apparatus with the two vertical legs separated by a horizontal filter tube and fitted with two 8 mm Teflon stopcocks, was loaded in one leg (under argon), with zirconium tetrachloride (3.0 g), and two glass-covered magnetic stir bars. The $ZrCl_4$ (Alfa-Ventron Reactor grade), was purified by vacuum sublimation, and powdered by grinding under argon, before use. The apparatus was then taken out of the argon drybox and attached to a source of UHP argon. To the othe leg of the apparatus was added via a syringe, n-butyllithium (Alfa-Ventron) (60 mL of a 2.2 M solution in n-hexane), under cover of argon. The portion of the apparatus containing the $ZrCl_4$ was then cooled to −196° C. with liquid nitrogen and the butyllithium solution was added gradually by passing it through the filter frit. When addition of butyllithium was complete the solution was allowed to warm to room temperature,

TABLE 1

Binary Hydrides as Benzene Hydrogenation Catalysts

| Run No. | Hydride | Benzene (mL) | Pressure kPa (gage) | Temp. (°C.) | Time hours | Benzene Conv. 5.8m % | Selectivity to cyclohexane % |
|---|---|---|---|---|---|---|---|
| A | $TiH_2$ (a)* | 5 | 982–479 | 150–153 | 16 | 22.8 | n.d. |
| B | $ZrH_2$ (b) | 2.5 | 900–748 | 82–105 | 7 | 8.2 | 14 |
| C | $ZrH_2$ (a)* | 4 | 962–517 | 121–130 | 5.5 | 32 | n.d. |
| D | $ZrH_2$ (c) | 2.0 | 896–862 | 97–103 | 3 | 2.7 | 24 |
| E | $HfH_2$ (b) | 2.4 | 903–746 | 83–99 | 2.8 | 10 | 20 |
| F | NbH* | 2.5 | 1000–882 | 180 | 14.5 | 7.3 | n.d. |
| G | $LaH_3$ | 2.5 | 986 | 170–176 | 16.5 | 0.4 | 3 |
| H | $UH_3$ | 2.5 | 970 | 182 | 14.5 | 1 | 10 |

(a) Commercial $TiH_2$, $ZrH_2$ from ROC/RIC
(b) atomic grade Zr + $H_2$, or Hf + $H_2$
(c) Prep. of $ZrH_2$ (atomic grade) + $H_2$ in molybdenum boat. Spectrographic analysis of $ZrH_2$: <0.05% of Ni, Mo, Co, Fe; no trace Pd, Pt.n.d. = none detected
*200 mg hydride. All other runs were with 100 mg hydride.

with stirring. It was subsequently heated to 70° C. (under a slow flow of argon) at ambient pressure, for 16 hours. A dark, gray-black solid precipitated. The supernatant liquid was filtered into the other leg of the apparatus and the remaining precipitate was worked repeatedly with fresh n-hexane. Evaporation of the last traces of n-hexane in vacuum, left a dry gray-black (highly pyrophoric!) solid catalyst which was stored under argon. Yield 4.5 g. The preparation worked equally well using the equivalent amount of zirconium tetrabromide instead of the tetrachloride.

A similar preparation was also carried out using benzene, instead of n-hexane as the diluent and reaction medium. Sec-butyllithium was also used as a reductant, although with this reagent, a slightly less active "$ZrH_x$" catalyst was obtained.

EXAMPLE 4

Preparation of a Copper Modified $ZrH_x$

A glass tube (about 4 cm × 0.22 cm O.D.) attached via a constriction to a Teflon vacuum stopcock was loaded (under argon) with a mixture of pure sublimed zirconium tetrachloride (4.0 g) and anhydrous copper (I) chloride, (Cerac, 99.99% CuCl), and a $\frac{3}{8}"\times\frac{3}{8}"$ (9.5 mm × 9.5 mm) glass covered magnetic stir bar. The tube was then evacuated and sealed off at the entrance with a gas-oxygen flame. The sealed tube was placed in a steel pressure container, and heated to 430°–450° C. with magnetic stirring, for 3 hours. To prevent rupturing of the glass tube from the internal pressure of $ZrCl_4$ vapor, argon (ranging from 1.7 to 3 MPa pressure) was admitted into the steel container. On cooling, a light green solid was recovered. The latter was finely powdered and reacted with butyllithium (2.0 g of the $ZrCl_4$/CuCl melt + 40 ml of 2.2 M butyllithium), as in Example 1. Recovered: 2.6 grams of a dark gray (pyrophoric) powdered solid catalyst.

EXAMPLE 5

Kinetics of Benzene Hydrogenation with $ZrH_x$ Catalysts

A one-inch (2.5 cm) I.D. glass pressure tube (Fisher & Porter Co.), containing a $\frac{3}{8}"\times\frac{3}{8}"$ (9.5 mm × 9.5 mm) magnetic stir bar was loaded under argon with the $ZrH_x$ (200 mg) catalyst (prepared as described in Example 3). The pressure tube was sealed with a steel head, fitted with a silicone rubber septum, and a connector to a vacuum/pressure steel manifold. To the manifold were attached a pressure gage and a source of hydrogen at constant pressure. The reactor tube was then charged with benzene (4 mL) and heated under $H_2$ with stirring for 16 hours. After this, the reactor was cooled to room temperature and the $H_2$ and remaining liquid ($C_6H_{12}$) were removed under vacuum. Benzene (2 mL, 1.91 g) and diethyl ether (2 mL, 1.43 g) were then distilled over the ($H_2$-pretreated) catalyst. Hydrogen was admitted and the reaction was heated to 100° C., under constant $H_2$ pressure (860 kPa). After an initial equilibration, samples were taken every 20 minutes and analyzed for $C_6H_{10}$, $C_6H_{10}$ and $C_6H_{12}$, by gas chromatography. The initial selectivity for cyclohexane was 86%; dropping to 47%, at 20% conversion of benzene.

The preceeding experiment is summarized as Run J in Table 2. Other similar examples with catalysts of Examples 3 and 4 and various (catalyst modifier) additives at levels of 0.5, 1 or 2 mL are also summarized in Table 2.

TABLE 2

| Run | Catalyst Example (mg) | Additive (mL) | Initial Selectivity | % Selectivity at 20% Conversion | Rate* |
|---|---|---|---|---|---|
| H | 3 (200) | — | 47.5 | 6 | 6.8 |
| I | 3 (200) | EE(2) | 87 | 42 | 9.0 |
| J | 3 (200) | EE(2) | 86 | 47 | 11 |
| K | 4 (280) | EE(2) | 89 | 35** | 2.9 |
| L | 4 (280) | PE(1) | 90 | 25 | 4.4 |
| M | 4 (200) | IPE(0.5) | 80 | 22 | 4.1 |
| N | 4 (200) | THF(1) | 84 | 20** | 1.7 |
| O | 3 (200) | TEA(0.5) | 76 | 17 | 3.8 |

EE = ethyl ether
PE = n-propyl ether
IPE = isopropyl ether
THF = tetrahydrofuran
TEA = triethylamine
*rate expressed as a pseudofirst order rate constant in hour$^{-1}$
**- extrapolated

What is claimed is:

1. A process of producing cyclohexene or alkylcyclohexene which comprises reacting liquid benzene or alkylbenzene with hydrogen gas in the presence of a catalytic amount of a solid carbonaceous group IVa metal hydride.
   said solid carbonaceous group IVa metal hydride having been produced by reacting a group IVa metal halide with a hydrocarbon solution of an alkyllithium or aryllithium at a temperature between about 0° and about 120° C., recovering the solid carbonaceous product, and reacting the solid carbonaceous product with hydrogen to produce said solid carbonaceous Group IVa metal hydride.

2. The process of claim 1 wherein the Group IVa metal halide is a zirconium halide.

3. The process of claim 1 wherein a copper halide is also reacted with the Group IVa metal halide and hydrocarbon solution of alkyllithium or aryllithium.

4. The process of claim 1, 2 or 3 wherein the reaction between benzene or alkylbenzene and hydrogen is conducted in the presence of the catalyst and of a co-catalyst selected from the group consisting of aliphatic tertiary amines, dialkyethers, cycloalkylethers of at least five ring carbons and cyclic unsaturated tertiary amines.

5. The process of claim 4 wherein benzene is reacted with hydrogen gas.

6. The process of claim 5 wherein the reaction product contains at least 10 mols of cyclohexene per mol of cyclohexane.

7. A process of producing cyclohexene or alkylcyclohexene which comprises reacting liquid benzene or alkylbenzene with hydrogen gas in the presence of a solid catalyst comprising a group IVa metal hydride selected from the group consisting of zirconium hydride, titanium hydride and hafnium hydride.

8. The process of claim 7 wherein the metal hydride is zirconium hydride.

9. The process of claim 8 wherein the catalyst is $ZrH_2$ and the reaction is conducted with sufficient agitation to expose fresh catalyst surface.

10. The process of claim 7 wherein benzene is reacted with hydrogen gas.

11. The process of claim 10 wherein the reaction product contains at least 10 mols of cyclohexene per mol of cyclohexane.

12. The process of claim 7 or 8 or 9 or 10 or 11 wherein the reaction between benzene or alkylbenzene and hydrogen is conducted in the presence of the catalyst and of a co-catalyst selected from the group consisting of aliphatic tertiary amines, dialkyethers, cycloalkylethers of at least five ring carbons and cyclic saturated tertiary amines.

* * * * *